United States Patent [19] [11] Patent Number: 5,918,976
Hashimoto et al. [45] Date of Patent: Jul. 6, 1999

[54] MIXING METHOD

[75] Inventors: Katuya Hashimoto; Toshiyuki Hagiwara; Masami Akiyama, all of Hino; Kunihisa Tabuchi; Nobuhiko Sano, both of Shizuoka-ken, all of Japan

[73] Assignees: Konica Corporation, Tokyo; Konica Chemical Corporation, Shizuoka-ken, both of Japan

[21] Appl. No.: 08/933,996

[22] Filed: Sep. 19, 1997

Related U.S. Application Data

[63] Continuation of application No. 08/523,237, Sep. 5, 1995, abandoned.

[30] Foreign Application Priority Data

Sep. 6, 1994 [JP] Japan ................................. 6-236034

[51] Int. Cl.⁶ ........................... B01F 5/10; B01F 15/02
[52] U.S. Cl. ..................... 366/132; 366/137; 366/151.1; 366/174.1; 366/336; 422/229; 422/224; 422/108
[58] Field of Search ............................ 366/150.1, 151.1, 366/142, 132, 136, 137, 131, 144, 145, 146, 140, 336, 174.1; 137/3, 5, 6, 93; 422/62, 67, 68.1, 70, 82, 82.12, 105, 108, 109, 110, 111, 132, 135, 220, 224, 229, 235, 260

[56] References Cited

U.S. PATENT DOCUMENTS

| | | | |
|---|---|---|---|
| 3,539,116 | 11/1970 | Podmore | 366/136 |
| 3,653,820 | 4/1972 | Kobs et al. | 422/62 |
| 3,661,364 | 5/1972 | Lage | 366/136 |
| 4,312,594 | 1/1982 | Woodle | 366/150.1 |
| 4,319,848 | 3/1982 | Lambertini et al. | 366/136 |
| 4,332,590 | 6/1982 | Smith | 422/62 |
| 4,370,046 | 1/1983 | Van Bouwel et al. | 366/136 |
| 4,403,866 | 9/1983 | Falcoff et al. | 366/136 |
| 4,407,431 | 10/1983 | Hutter, III | 366/137 |
| 4,572,819 | 2/1986 | Priddy et al. | 422/62 |
| 4,622,188 | 11/1986 | Adamich et al. | 422/62 |
| 4,664,528 | 5/1987 | Rodgers et al. | 366/137 |
| 4,823,987 | 4/1989 | Switall | 366/132 |
| 4,893,937 | 1/1990 | Braun | 366/136 |
| 4,974,964 | 12/1990 | Yoshihara et al. | 366/136 |
| 5,052,486 | 10/1991 | Wilson | 366/136 |
| 5,197,800 | 3/1993 | Saidman et al. | 366/136 |
| 5,260,026 | 11/1993 | Feld et al. | 422/62 |
| 5,380,485 | 1/1995 | Takahashi et al. | 422/62 |
| 5,478,529 | 12/1995 | Sobata et al. | 422/62 |

Primary Examiner—Tony G. Soohoo
Attorney, Agent, or Firm—Finnegan, Henderson, Farabow, Garrett & Dunner, L.L.P.

[57] ABSTRACT

Disclosed is a process for forming a compound by mixing at least two components, which comprises the steps of:
  circulating a specific component along a circulation route; and
  mixing the specific component with a second component different from the specific component by flowing the second component different from the specific component in the middle of the circulation route under specific mixing conditions to form a compound during circulation,
wherein the mixing conditions are controlled so that the mixing conditions are changed accompanied with increase in a formation amount of the compound.

4 Claims, 7 Drawing Sheets

Reactivity (mole %)

MIXING METHOD

This application is a continuation of application Ser. No. 08/523,237, filed Sep. 5, 1995, now abandoned.

BACKGROUND OF THE INVENTION

This invention relates to a mixing method of synthesizing a compound by reacting at least two components.

In a light-sensitive material, various compounds have been used. For example, active methylene compounds represented by acetoacetic acid ester, acetoacetic anilide, malonic acid ester and dimedone are compounds useful as an intermediate of a compound used for a photographic light-sensitive material. Further, these compounds have been used as an intermediate of an agricultural chemical, a medicine, a dye or a pigment. Also, halides of these compounds are important compounds. The active methylene compounds can be easily halogenated by reacting with a halogenating reagent such as chlorine, bromine, sulfuryl chloride or N-chlorosuccinimide.

When sulfuryl chloride is used as a halogenating reagent, as a solvent for the active methylene chloride, there may be mainly used a halogen type solvent such as chloroform, carbon tetrachloride, methylene chloride, dichloroethane, trichloroethane or tetrachloroethane.

However, there is a fear of influence of this kind of the halogen type solvent on human bodies so that it has been proposed to use a solvent other than a halogen type solvent as described in Japanese Provisional Patent Publication No. 230638/1992.

As described in Example 1 of Japanese Provisional Patent Publication No. 230638/1992, when the active methylene compound is batchwisely halogenated with a halogenating reagent (sulfuryl chloride) by mixing both of them in a vessel by using a stirrer, for example, a 2,2-dichloro compound is formed as a by-product. Further, when ethyl acetate is used as a solvent in place of the halogen type solvent as shown in Example 1 of the above publication, a generation amount of the above by-product is the same level in small scale production, but said amount is larger in large scale production, as compared with the case of using the halogen type solvent. As a result, lowering in yield of a desired halide of the active methylene compound is brought about, and also lowering in quality is brought about. The by-product has the same chemical structure as that of the desired compound so that it is difficult to separate the by-product in subsequent steps. Therefore, as to a photographic starting compound high quality of which is absolutely required, it has been demanded to reduce an amount of a by-product as far as possible. The reaction rate of the above halogenation is as extremely rapid as 10 minutes or shorter in terms of a half-life thereof.

The cause for generating the by-product during synthesis is considered that when the desired compound is synthesized by chlorinating the active methylene compound with sulfuryl chloride, the desired compound formed and sulfuryl chloride exist locally with high concentrations so that a reaction from the desired compound to the by-product proceeds easily. When the reaction is carried out in a reaction system in which a solvent is used in a smaller amount and the active methylene compound is used with high concentration in order to obtain high productivity, a reaction mixture has an increased viscosity, and as a result, diffusion is inhibited so that the desired compound and sulfuryl chloride exist locally with high concentrations, whereby a reaction of the desired compound and sulfuryl chloride is accelerated to generate the by-product more easily.

In order to effect sufficient diffusion in a reaction system, it is necessary to increase the rotary number of a stirrer to carry out stirring sufficiently. As to increase in the rotary number of a stirrer, there is a mechanical limit, and also a necessary amount of energy is increased.

In order to solve the above problems, the present inventors have proposed to carry out a reaction while mixing a first reaction solution and a second reaction solution successively by using a static mixing device in Japanese Provisional Patent Publication No. 249583/1993.

By the above reaction method, generation of a by-product can be suppressed and a production cost can be decreased. However, it is necessary to control a flow rate precisely so that an equipment cost is large and there is a limit in decreasing the production cost. Further, the by-product exerts great influence on quality of the desired compound so that in order to further improve said quality, it has been demanded to reduce an amount the by-product by 0.1% order.

SUMMARY OF THE INVENTION

An object of the present invention is to provide a mixing method by which a desired compound can be obtained with high yield by suppressing a generation amount of a by-product while reducing a production cost.

The above object of the present invention can be accomplished by (1) a process for forming a compound by mixing at least two components, which comprises the steps of:
  circulating a specific component along a circulation route; and
  mixing the specific component with a second component different from the specific component by flowing the second component different from the specific component in the middle of the circulation route under specific mixing conditions to form a compound during circulation,
  wherein the mixing conditions are controlled so that the mixing conditions are changed accompanied with increase in a formation amount of the compound, (2) the process of the above (1) wherein a static mixing device is arranged in the circulation route, (3) the process of the above (1) wherein one of the mixing conditions is a flow velocity of the second component different from the specific component to be introduced into the circulation route, (4) the process of the above (1) wherein one of the mixing conditions is a temperature of the circulation route, (5) the process of the above (1) wherein one of the mixing conditions is a circulation velocity of the components in the circulation route, (6) the process of the above (1) which further comprises a step of detecting data showing a formation amount of the compound formed in the circulation route to control the mixing conditions by the detected data, (7) the process of the above (1) wherein the specific component circulating through-the circulation route is dissolved or dispersed in a solvent, (8) the process of the above (1) wherein the second component different from the specific component is dissolved or dispersed in a solvent, (9) the process of the above (1) wherein the second component different from the specific component has a half-life of 10 minutes or shorter, (10) the process of the above (9) wherein the compound is a starting material of a light-sensitive material or an intermediate of a light-sensitive material, (11) the process of the above (10) wherein the specific component is an active methylene compound and the second component different from the specific component is a halogenating reagent, or the specific component is a halogenating reagent and the second component different from the specific component is an active methylene compound, (12) the process of the above (10) wherein the specific component is a compound containing an active methylene group, and the second component different from the specific component is a halogenating reagent, and (13) the process of the above (1) which further comprises steps of:
  transferring the components circulated in the circulation route including the formed compound to a different vessel; and
  charging the second component different from the specific component into the different vessel and mixing the components in said vessel.

DESCRIPTION OF THE PREFERRED EMBODIMENTS

In the following, the mixing method of the present invention is explained in detail by referring to the drawings.

Figure 1:
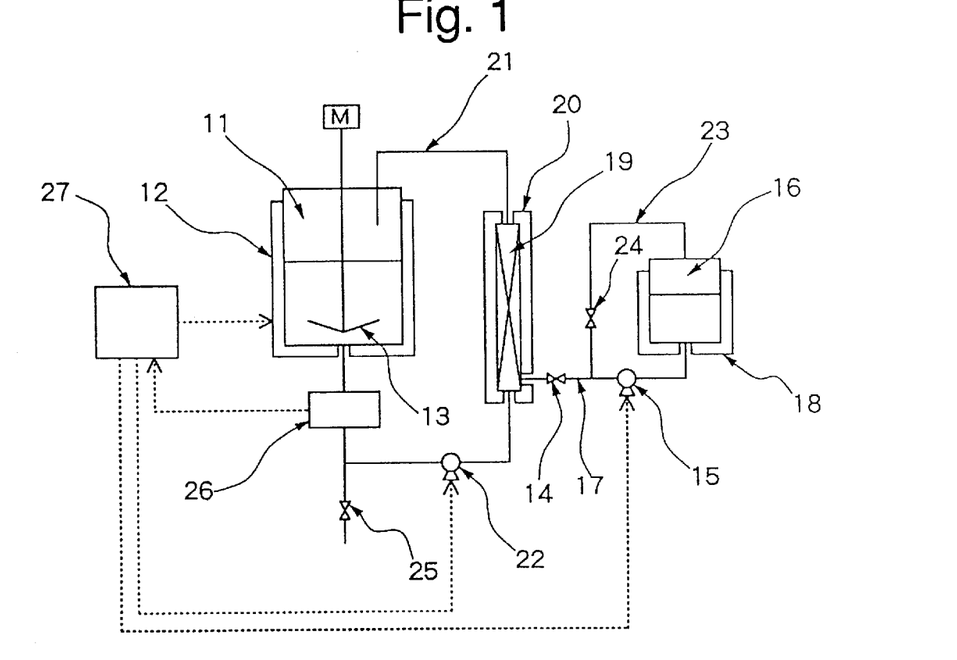
FIG. 1 is an illustrative view for illustrating the mixing method of the present invention.
Figure 2:
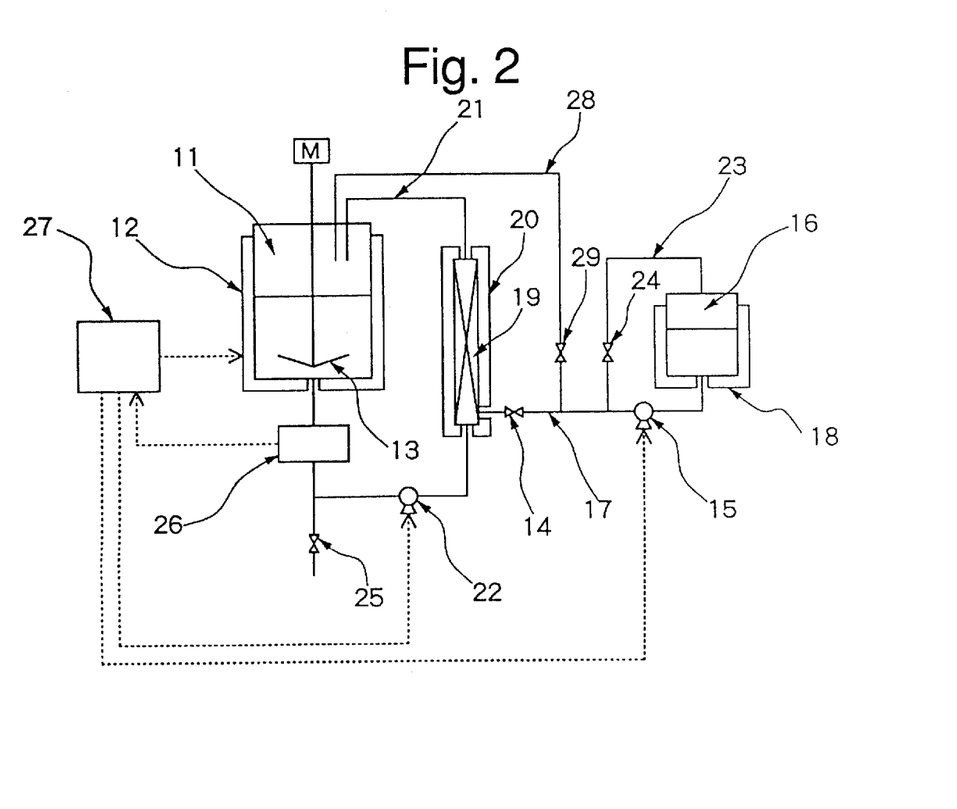
FIG. 2 is an illustrative view for illustrating the other mixing method of the present invention.

In FIG. 1 and FIG. 2, reference numeral 11 shows a storage tank, 12 shows a jacket, 13 shows a stirrer, 14 shows a valve, 15 shows a constant flow rate pump, 16 shows a storage tank, 17 shows a flow passage, 18 shows a jacket, 19 shows a static mixing device, 20 shows a jacket, 21 shows a flow passage, 22 shows a constant flow rate pump, 23 shows a flow passage, 24 shows a valve, 25 shows a discharge valve, 26 shows a reactivity-measuring device and 27 shows a controlling device. In FIG. 2, 28 shows a flow passage and 29 shows a valve.

In FIG. 1 and FIG. 2, a circulation system is constituted by the static mixing device 19 which is a mixing means, the flow passage 21, the storage tank 11 and the constant flow rate pump 22 so that a first specific component is circulated through the circulation system by the constant flow rate pump 22. The static mixing device 19 is equipped with the jacket 20 so that the static mixing device 19 can be heated or cooled. The storage tank 11 has the stirrer 13 internally thereof so that stirring can be carried out. Also, the storage tank 11 equipped with the jacket 12 externally thereof so that the storage tank 11 can be heated or cooled.

A second component which is the other component to be used for a synthetic reaction is stored in the storage tank 16 and charged into an upstream side of the static mixing device 19 through the flow passage 17 and the valve 14 by the constant flow rate pump 15. The storage tank 16 is equipped with the jacket 18 so that the storage tank 16 can be heated or cooled.

The reactivity-measuring device 26 measures reactivity which is a degree of mixing the first component circulating the circulation system with the second component and gives, a signal to the controlling device 27. By the signal from the reactivity-measuring device 26, the controlling device 27 controls mixing conditions of the second component.

The flow passage 23 is arranged for returning the second component to the storage tank 16 until a flow rate charged from the constant flow rate pump 15 becomes stable. The flow passage 23 is equipped with the valve 24.

In FIG. 2, the flow passage 28 is arranged for conveying the second component from the storage tank 16 to the storage tank 11 and used when the latter half of the reaction is carried out batchwisely in the storage tank 11.

In FIG. 2, the latter half of the reaction carried out batchwisely is carried out in the storage tank 11, but there may be provided another tank where the batchwise reaction is carried out.

The static mixing device 19 is not particularly limited, and there may be used various conventionally known static mixing devices such as a static mixer type mixing device, a nozzle type mixing device, an orifice type mixing device and an injector type mixing device.

Figure 4:
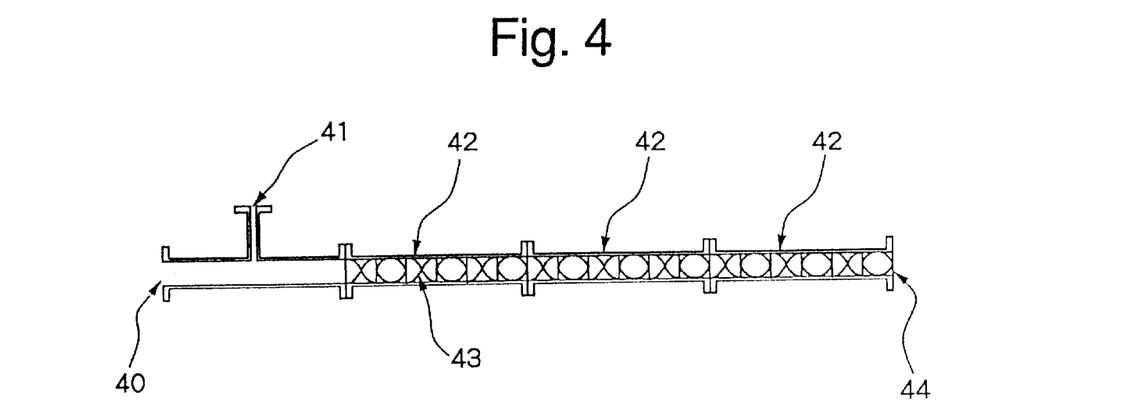
FIG. 4 is a schematic view showing one example of the static mixing device used in the present invention.
Figure 5:
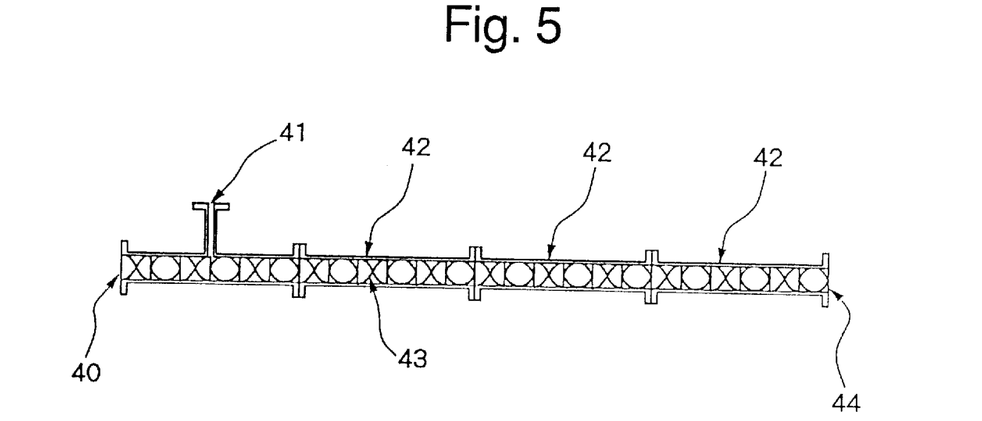
FIG. 5 is a schematic view showing another example of the static mixing device used in the present invention.
Figure 6:
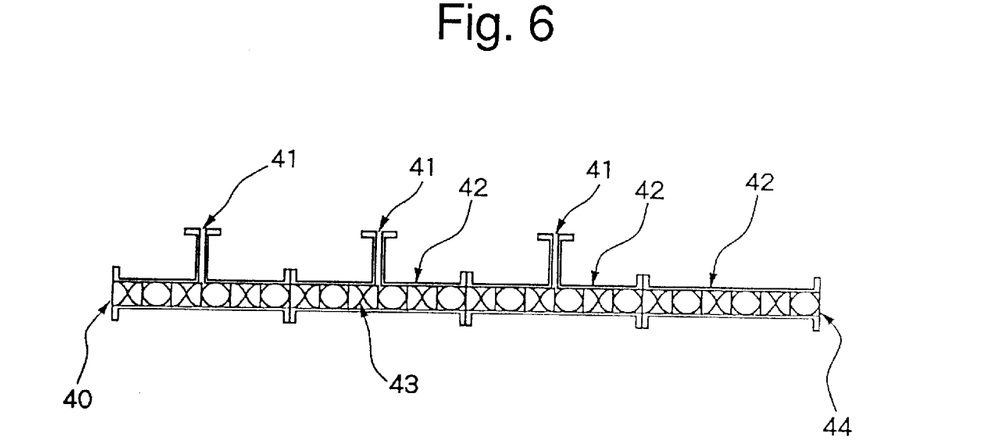
FIG. 6 is a schematic view showing another example of the static mixing device used in the present invention.
Figure 7:
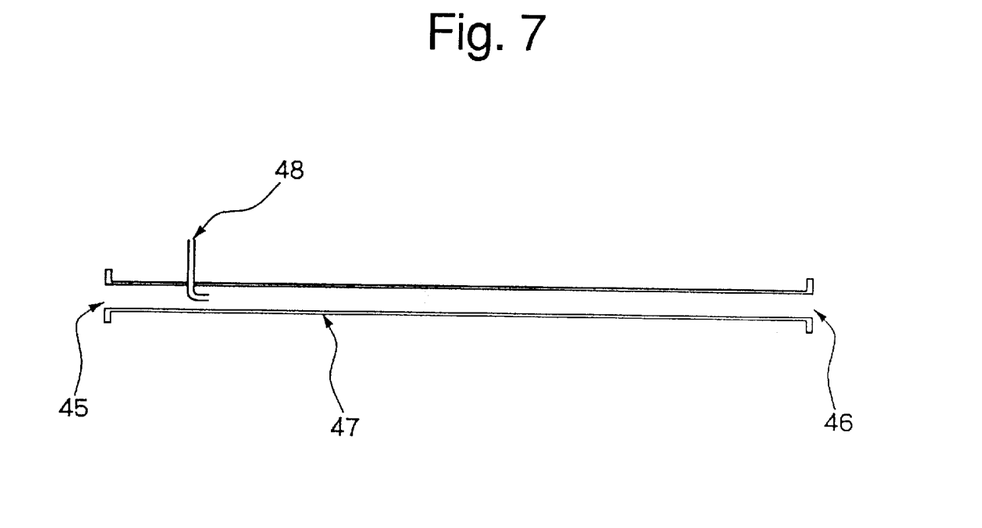
FIG. 7 is a schematic view showing another example of the static mixing device used in the present invention.

FIG. 4 to FIG. 6 show examples of the static mixer type mixing device, and FIG. 7 shows an example of the nozzle type mixing device.

In FIG. 4 to FIG. 6, 40 shows an inlet, 41 shows a T-shaped tube, 42 shows a static mixer, 43 shows an element and 44 shows an outlet. The first component is supplied from the inlet 40, passed through the static mixers 42, mixed and reacted with the second component supplied from the T-shaped tube 41 to form a predetermined compound and discharged from the outlet 44. In the static mixer 42, a large number of the elements 43 having such a shape that an end of a plate is twisted by 90° are arranged so that mixing is carried out when a liquid is passed through the elements 43.

FIG. 4 shows an example in which the T-shaped tube 41 is arranged on a tube having no element 43, FIG. 5 shows an example in which the T-shaped tube 41 is arranged on the static mixer 42, and FIG. 6 shows an example in which a large number of T-shaped tubes 41 are arranged on the static mixers 42. In the static mixer type mixing device shown in FIG. 6, plural second components can be supplied. These plural second components may be the same component or different components.

In FIG. 7, 45 shows an inlet, 46 shows an outlet, 47 shows a tube and 48 shows a L-shaped tube. The first component is supplied to the tube 47 from the inlet 45, mixed and reacted with the second component supplied from the L-shaped tube 48 in the tube 47 and discharged from the outlet 46.

In FIG. 1, the first component is supplied to the storage tank 11 and circulated through the static mixing device 19 by driving the constant flow rate pump 22. The second component is supplied to the storage tank 16. When a flow rate circulating through the static mixing device 19 becomes stable, the constant flow rate pump 15 is driven and the valve 14 is opened to supply the second component in an amount necessary for the synthetic reaction, at an upstream position of the static mixing device 19 or at a middle position of the static mixing device 19, whereby the reaction is carried out. After mixing of necessary amounts of the components is completed, all of the components are discharged from the valve 25.

In the mixing method of the present invention, the storage tank 11 is not essentially required.

While the second component is mixed and reacted with the first component, the reactivity of the first component is measured by the reactivity-measuring device 26 to control the mixing conditions under which the second component is mixed with the first component.

In FIG. 2, the first component is supplied to the storage tank 11 and circulated through the static mixing device 19 by driving the constant flow rate pump 22. The second component is supplied to the storage tank 16. When a flow rate circulating through the static mixing device 19 becomes stable, the constant flow rate pump 15 is driven and the valve 14 is opened to supply the second component in an amount which is less than an amount necessary for the synthetic reaction, at an upstream position of the static mixing device 19 or at a middle position of the static mixing device 19 so that a first stage reaction is carried out. While the second component is mixed and reacted with the first component, the reactivity of the first component is measured by the reactivity-measuring device 26 to control the mixing conditions under which the second component is mixed with the first component. Then, the valve 14 is closed, circulation through the static mixing device 19 is terminated and the valve 29 is opened to charge the remaining second component into the storage tank 11 through the flow passage 21 so that a second stage reaction proceeds. In the storage tank 11, the stirrer 13 is arranged, by which stirring is carried out while the reaction proceeds. After the reaction is completed, all of the components are discharged from the valve 25.

In the mixing method of the present invention, the storage tank 11 is not essentially required for carrying out the first stage reaction.

While the second component is charged to proceed the first stage reaction, the reactivity of the first component is measured by the reactivity-measuring device 26 to control the mixing conditions under which the second component is mixed With the first component.

The reactivity of the first component can be determined directly by, for example, sampling the reaction mixture and analyzing it by high performance liquid chromatography. When viscosity is changed depending on the reactivity, the reactivity can be also determined by measuring viscosity. If the reactivity of the first component to the second component mixed under specific conditions is determined previously, the reactivity can be determined by a mixing amount of the second component as long as mixing is carried out under the specific conditions.

As control of the conditions under which the second component is added, which is carried out accompanied with increase in a formation amount of the desired compound which is a predetermined compound formed in the circulation system, there may be mentioned, for example, (1) control of a flow velocity (addition rate) of the second component to be charged at an upstream position of the static mixing device or in the middle of the static mixing device;
(2) control of a temperature of the circulation system; and
(3) control of a circulation velocity of the circulation system.

These controls may be carried out by successively or step-wisely increasing or decreasing a flow velocity of the second component to be charged at an upstream position of the static mixing device or in the middle of the static mixing device; successively or stepwisely elevating or lowering a temperature of the circulation system; and successively or stepwisely increasing or decreasing a circulation velocity of the circulation system, accompanied with increase in the reactivity.

These controls are actually carried out accompanied with increase in the reactivity, by changing a flow velocity of the second component to be charged at an upstream position of the static mixing device or in the middle of the static mixing device according to a certain function; changing a temperature of the circulation system according to a certain function; and changing a circulation velocity of the circulation system according to a certain function.

The above control of the conditions under which the second component is charged may be selected so that optimum results can be obtained in the respective synthetic reactions. An optimum control can be selected by carrying out a simple experiment.

Further, the above control of the conditions may specifically be carried out by the following systems:

(1) the conditions such as a temperature, a flow velocity and a circulation velocity are controlled by storing, in a memory, data for changing the conditions such as a temperature, a flow velocity and a circulation velocity as a time or a generation amount is changed, and then inputting a time or a generation amount and also reading data from the memory; and
(2) the conditions such as a temperature, a flow velocity and a circulation velocity are controlled by detecting a state of a reaction and carrying out arithmetic processing based on detected values at an arithmetic processing section (in the arithmetic processing section, an arithmetic circuit or a program by a software is used).

The first component and the second component may comprise one compound or two or more compounds, respectively. When the second component comprises two or more compounds, the static mixer type mixing device shown in FIG. 6 is used as the static mixing device 19, and the respective compounds may be charged from the respective T-shaped tubes 41, or the two or more compounds may be charged simultaneously.

In the present invention, the first component and the second component may be used by dissolving or dispersing them in a solvent.

As the solvent, there may be mentioned, for example, a halogen type solvent such as chloroform, carbon tetrachloride, methylene chloride, dichloroethane, trichloroethane and tetrachloroethane; an ester type solvent such as ethyl acetate, methyl acetate, butyl acetate, methyl propionate and ethyl propionate; an aromatic hydrocarbon type solvent such as benzene, toluene and xylene; an aliphatic hydrocarbon type solvent such as n-hexane, n-heptane and isooctane; an ether type solvent such as diethyl ether, diiso-propyl ether, tetrahydrofuran and dioxane; a ketone type solvent such as acetone, methyl ethyl ketone and methyl isobutyl ketone; and a nitrile type solvent such as acetonitrile and propionitrile. These solvents may be used as a mixture of two or more of them.

The mixing method of the present invention can be used for synthesizing any compound, and formation of a by-product can be reduced. Therefore, the object of the present invention is to obtain a compound with high purity. The mixing method of the present invention is suitably used for synthesizing a compound which is difficult to be purified since a by-product is similar to a desired compound to be obtained by synthesis.

The mixing method of the present invention can reduce generation of a by-product so that it can be preferably used for synthesizing an intermediate of a compound used for a photographic light-sensitive material, by substituting one of hydrogen atoms at active points of an active methylene compound or the like by a halogen atom.

In the following, compounds which can be halogenated by the mixing method of the present invention are described.

As the compound which can be halogenated by the mixing method of the present invention, there may be mentioned, for example, an active methylene compound. The active methylene compound is a compound containing saturated hydrocarbon bonded to an unsaturated functional group such as a nitro group, a carbonyl group, a sulfone group, a cyano group, a sulfinyl group, an imino group and a phenyl group, preferably having an acidity (a pKa value) of 4 to 17. The pKa value of the active methylene compound is described in Herbert O. House, "MODERN SYNTHETIC REACTIONS", Second Edition, p. 428 (published by Hirokawa Shoten) and Japanese Provisional Patent Publications No. 13041/1975 and No. 151937/1981. As the active methylene compound having a pKa value in the range of 4 to 17, there may be mentioned an aliphatic nitro compound (e.g., dinitromethane, nitroethane and nitromethane), a cyanoacetic acid compound (e.g., methyl cyanoacetate, ethyl cyanoacetate, cyanoacetic anilide and cyanoacetyl coumarone), an aliphatic dicyano compound (e.g., malonodinitrile), a β-diketone compound (e.g., acetylacetone, benzoylacetone and dimedone), a β-ketoacetic acid compound (e.g, methyl acetoacetate, ethyl pivaloylacetate, methyl benzoylacetate, acetoacetic anilide, pivaloylacetic anilide and benzoylacetic anilide), a dicarboxylic acid compound (e.g., diethyl malonate and malonic dianilide) and a heterocyclic compound (e.g., 5-pyrazolone and pyrazoloazole).

As the active methylene compound which is halogenated by the mixing method of the present invention, there may be mentioned a β-ketoacetic acid compound represented by the following formula (1) and a pyrazolotriazole compound represented by the following formula (2) or (3).

(1)

In the formula (1), $R_1$ represents an alkyl group, a cycloalkyl group or an alcohol group; X represents a hydrogen atom, a halogen atom, an alkyl group or an alkoxy group; $R_2$ represents a hydrogen atom or a substituent; and m represents an integer of 0 to 4. When m is 2 or more, $R_2$'s in the number of m may be the same or different.

The compound represented by the formula (1) may be a compound in which $R_1$, $R_2$ or X is a divalent, trivalent or tetravalent linking group, which is a dimer, a trimer or a tetramer of the compound represented by the formula (1).

The formula (1) is further explained in detail. $R_1$ is preferably a straight or branched alkyl group having 1 to 30 carbon atoms, a cycloalkyl group or a phenyl group, more preferably a tertiary alkyl group or a 4-alkoxyphenyl group, most preferably a t-butyl group or a 4-methoxyphenyl group. These respective groups may have a substituent. As the substituent, there may be mentioned a halogen atom, an alkyl group, an aryl group, an alkoxy group, an aryloxy group, an alkylthio group, an arylthio group, a carbamoyl group, a sulfamoyl group, an acylamino group, a sulfonamide group, an alkyloxycarbonyl group, a nitro group, a cyano group, a hydroxyl group, an amino group, an alkylamino group and an arylamino group.

X is preferably a hydrogen atom, a halogen atom or an alkoxy group, particularly preferably a chlorine atom or an alkoxy group having 1 to 24 carbon atoms. The alkoxy group may have a substituent, and as the substituent, there may be mentioned the exemplary substituents for $R_1$ described above.

As the substituent represented by $R_2$, there may be mentioned, for example, a halogen atom (e.g., a fluorine atom and a chlorine atom), an alkyl group having 1 to 20 carbon atoms, an aryl group, an alkoxy group, an aryloxy group, an acylamino group, a sulfonamide group, a carbamoyl group, a sulfamoyl group, an acyloxy group, an amino group (e.g., ethylamino and anilino), an alkylthio group, an ureido group, a sulfamoylamino group, a cyano group, an alkoxycarbonyl group, an alkyloxycarbonylamino group, an imide group, an alkylsulfonyl group, an arylsulfonyl group and a heterocyclic group. These group may further have a substituent, and as the substituent, there may be mentioned the exemplary substituents for $R_1$ described above.

$R_2$ is preferably an acylamino group, a sulfonamide group, an alkoxycarbonyl group, a sulfamoyl group or a carbamoyl group.

The compound represented by the formula (1) may be a compound which is a dimer, a trimer or a tetramer thereof as described above, but preferably a monomer or a dimer.

The β-ketoacetic acid compound represented by the formula (1) can be synthesized easily by a synthetic method described in U.S. Pat. No. 3,384,657 and Japanese Provisional Patent Publications No. 30127/1981, No. 206385/1984 and No. 123047/1988.

(2)

(3)

In the formula (2) and the formula (3), $R_3$ and $R_4$ each represent a hydrogen atom or a substituent. The substituent represented by $R_3$ or $R_4$ is not particularly limited, and there may be representatively mentioned groups of alkyl, aryl, anilino, acylamino, sulfonamide, alkylthio, arylthio, alkenyl and cycloalkyl. In addition, there may be mentioned a halogen atom, groups of cycloalkenyl, alkynyl, hetero ring, sulfonyl, sulfinyl, phosphonyl, acyl, carbamoyl, sulfamoyl, cyano, alkoxy, aryloxy, heterocyclic oxy, siloxy, acyloxy, carbamoyloxy, amino, alkylamino, imide, ureido, sulfamoylamino, alkoxycarbonyl, aryloxycarbonyl and heterocyclic thio, a spiro compound residue and a bridged hydrocarbon compound residue.

The alkyl group represented by $R_3$ or $R_4$ is preferably an alkyl group having 1 to 32 carbon atoms and may be a straight alkyl group or a branched alkyl group.

The pyrazolotriazole compound represented by the formula (2) or the formula (3) is described in "Journal of the Chemical Society", Perkin 1 (1977), pp. 2047 to 2052, U.S. Pat. No. 3,725,067 and Japanese Provisional Patent Publications No. 99437/1984, No. 42045/1983, No. 162548/1984, No. 171956/1984, No. 33552/1985, No. 43659/1985, No. 172982/1985, No. 190779/1985, No. 209457/1987 and No. 307453/1988 and can be synthesized by referring to synthetic methods described therein.

In the following, specific examples of the compound which can be halogenated by the mixing method of the present invention are shown.

(1)

(2)

(3)

(4)

(5)

(6)

(7)

(8)

(9)

(10)

(11)

(12)

(13)

(14)

(15)

(16)

(17)

-continued

(18)

(19)

(20)

(21)

(22)

(23)

(24)

(25)

-continued (26)

(27)

(28)

(29)

(30)

As the halogenating reagent which halogenates the above active methylene compound, a sulfuryl halide may be used. As the sulfuryl halide, sulfuryl chloride and sulfuryl chlorofluoride are preferred, and sulfuryl chloride is particularly preferred.

When the active methylene compound is halogenated, it is preferred to use a solvent. As the solvent which can be used, there may be mentioned a halogen type solvent such as chloroform, carbon tetrachloride, methylene chloride, dichloroethane, trichloroethane and tetrachloroethane; an ester type solvent such as ethyl acetate, methyl acetate, butyl acetate, methyl propionate and ethyl propionate; an aromatic hydrocarbon type solvent such as benzene, toluene and xylene; an aliphatic hydrocarbon type solvent such as n-hexane, n-heptane and iso-octane; an ether type solvent such as diethyl ether, di-iso-propyl ether, tetrahydrofuran and dioxane; a ketone type solvent such as acetone, methyl ethyl ketone and methyl isobutyl ketone; and a nitrile type solvent such as acetonitrile and propionitrile. These solvents may be used as a mixture of two or more of them.

The starting compound is dissolved in the above solvent and circulated through the circulation system having the static mixing device, and sulfuryl halide is charged from an upstream position of the static mixing device or in the middle of the static mixing device. The flow velocity the halogenating reagent is not particularly limited, but it is preferred to select the flow velocity so that high productivity can be obtained and a formulation amount of a by-product can be reduced.

The amount of the solvent to be used is preferably 1 to 100 times, more preferably 2 to 20 times in terms of weight based on the amount of the specific component, and said amount is preferably 0 to 100 times, more preferably 0 to 20 times in terms of weight based on the amount of the second component.

The reaction temperature is not particularly limited. However, if the temperature is too low, the reaction proceeds slowly, while if it is too high, a decomposition reaction proceeds. Therefore, the reaction temperature is preferably $-20°$ C. to $100°$ C., more preferably $-10°$ C. to $70°$ C.

The amount of sulfuryl halide to be used varies depending on a desired compound to be formed. For example, when a monohalogen compound is to be obtained, the amount of sulfuryl halide is preferably 0.5 to 1.5 mole, more preferably 0.8 to 1.2 mole per mole of the starting compound.

EXAMPLES

The present invention is described in detail by referring to Examples and Comparative examples, but the present invention is not limited by these Examples and Comparative examples.

In Examples and Comparative examples, Compound (A) represented by the following formula:

was chlorinated with sulfuryl chloride to synthesize a monochloro compound (Compound (B)).

In Examples and Comparative examples, reactivity was determined by sampling a reaction mixture and analyzing it by high performance liquid chromatography.

Example 1

A synthetic reaction was carried out by using the apparatus shown in FIG. 2. As the static mixing device 19, there was used a line mixer having the structure shown in FIG. 5 and having an inner diameter of 5 mm, a length of 150 mm, the number of elements being 18 and a distance from the inlet 40 to the T-shaped tube 41 of 20 mm.

In 35.4 l of chloroform was dissolved 20 kg of Compound (A) by heating to obtain 53.4 l of a chloroform solution containing Compound (A). The solution was supplied to the storage tank 11. The solution was cooled so as to have a temperature of 35 to 40° C. by stirring it by the stirrer 13 and passing cooling water through the jacket 12.

Then, by driving the constant flow rate pump 22 so that a flow rate of 1.3 l/min could be obtained, the above solution was circulated through the line mixer 19 and the flow passage 21 until the temperature and flow of the solution became stable. By opening the valve 24 and driving the constant flow rate pump 15 so that a flow rate of 9.1 ml/min could be obtained, sulfuryl chloride in the storage tank 16 was circulated through the flow passage 23 until the flow became stable. When the respective flows became stable, the valve 24 was closed and the valve 14 was opened to supply sulfuryl chloride to the line mixer 19 at a flow rate of 9.1 ml/min and also terminate supply of cooling water to the jacket 12. Also, a predetermined amount of cooling water was supplied to the jacket 20 of the line mixer 19 in accordance with the amount of the reaction mixture to cool the reaction mixture. When 1.6 kg (0.92 l) of sulfuryl chloride was supplied, the valve 14 was closed and the valve 24 was opened to terminate supply of sulfuryl chloride, and a first stage reaction was completed.

During the reaction, the reactivity of Compound (A) and the solution temperature of the storage tank 11 were measured.

Figure 8:
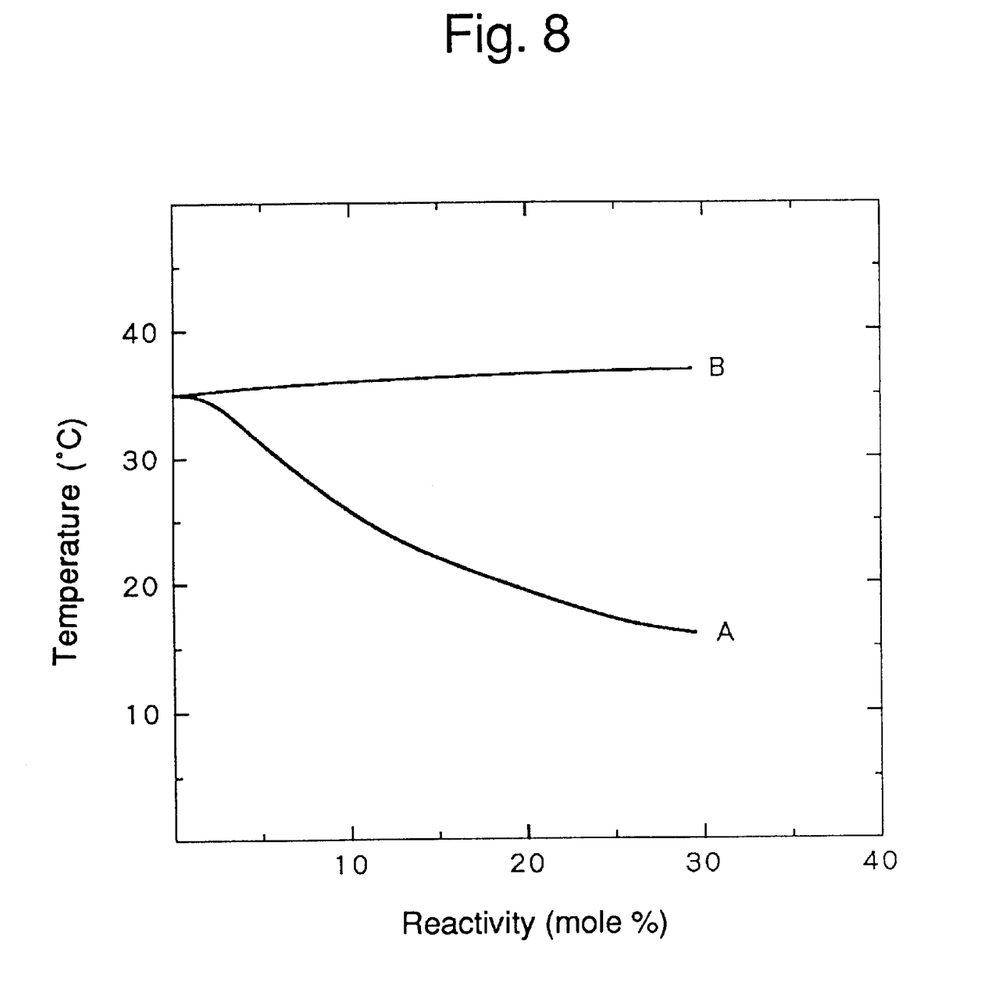
FIG. 8 is a view showing each relation between reactivity and a temperature of a circulation system in Example 1 and Comparative example 1—1.

When a relation between the reactivity of Compound (AY and the solution temperature of the storage tank 11 was plotted, the relation was shown by Curve A in FIG. 8.

After completion of the reaction, the resulting product was analyzed by high performance liquid chromatography to find that 68.4% of the residual starting compound, 29.3% of Compound (B) and 0.3% of the by-product were contained and the remainder was impurities contained in the starting compound.

The reaction mixture obtained was cooled to 15 to 20° C. By opening the valve 24 and driving the constant flow rate pump 15, sulfuryl chloride in the storage tank 16 was circulated through the flow passage 23 until the flow became stable. When the flow became stable, the valve 24 was closed and the valve 29 was opened to add 3.5 kg of sulfuryl chloride to the above reaction mixture stirred by the stirrer 13 and cooled to 15 to 20° C., through the flow passage 28 over 60 minutes, whereby a reaction was carried out batchwisely.

After completion of the reaction, the resulting product was analyzed by high performance liquid chromatography to find that 0.5% of the residual starting compound, 96.4% of Compound (B) and 1.1% of the by-product were contained and the remainder was impurities contained in the starting compound.

Comparative Example 1-1

A first stage reaction was carried out in the same manner as in Example 1 except for not supplying cooling water to the jacket 20 of the line mixer 19.

During the reaction, the reactivity of Compound (A) and the solution temperature of the storage tank 11 were measured. The solution temperature was substantially constant. When a relation between the reactivity of Compound (A) and the solution temperature of the storage tank 11 was plotted, the relation was shown by Curve B in FIG. 8.

After completion of the reaction, the resulting product was analyzed by high performance liquid chromatography to find that 69.0% of the residual starting compound, 28.7% of Compound (B) and 0.6% of the by-product were contained and the remainder was impurities contained in the starting compound.

Next, a reaction was carried out batchwisely in the same manner as in Example 1. After completion of the reaction, the resulting product was analyzed by high performance liquid chromatography to find that 0.8% of the residual starting compound, 95.8% of Compound (B) and 1.4% of the by-product were contained and the remainder was impurities contained in the starting compound.

Comparative example 1-2

Figure 3:
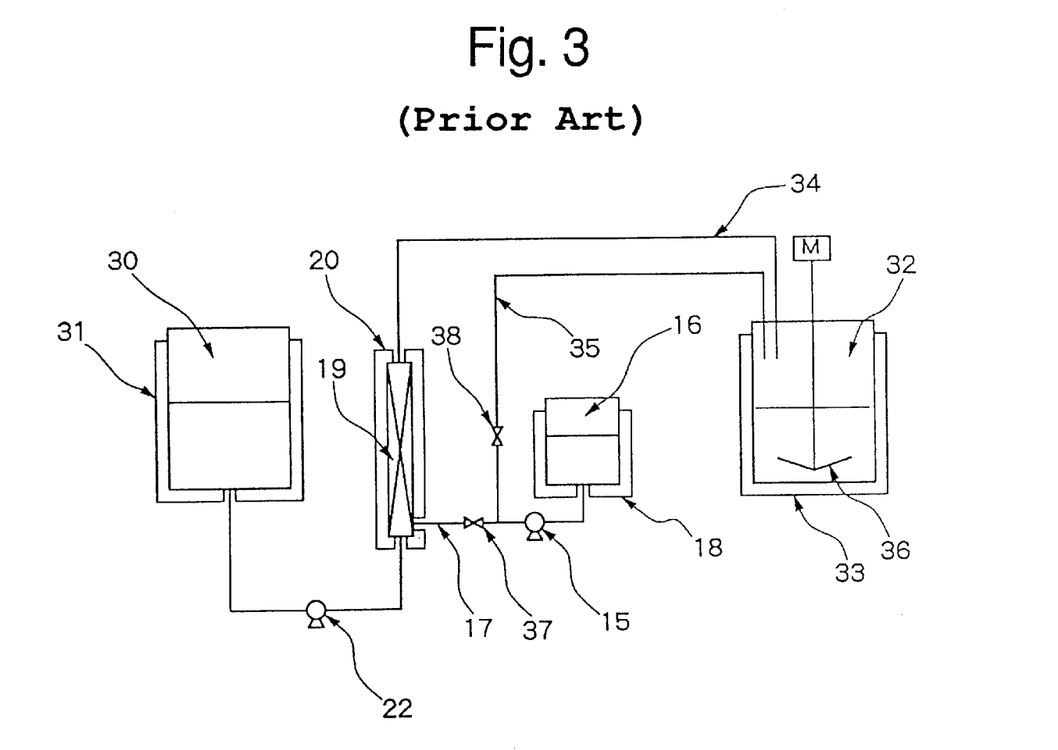
FIG. 3 is an illustrative view for illustrating a mixing method of Comparative example 1–2.

A synthetic reaction was carried out by using the apparatus shown in FIG. 3. As the static mixing device 19, there was used a line mixer having the structure shown in FIG. 5 and having an inner diameter of 5 mm, a length of 150 mm, the number of elements being 18 and a distance from the inlet 40 to the T-shaped tube 41 of 20 mm.

In 35.4 l of chloroform, 20 kg of Compound (A) was dissolved by heating to obtain 53.4 l of a chloroform solution containing Compound (A). The solution was charged into the storage tank 30. The solution was cooled so as to have a temperature of 35 to 40° C. by passing cooling water through the jacket 31.

Then, the above solution was supplied to the line mixer 19 by driving the constant flow rate pump 22 so that a flow rate of 1.3 l/min could be obtained. Simultaneously therewith, by opening the valve 37, closing the valve 38 and driving the constant flow rate pump 15, 1.6 kg (0.92 l) of sulfuryl chloride in the storage tank 16 was supplied to the line mixer 19 through the flow passage 17 at a flow rate of 21.5 ml/min. In the line mixer 19, Compound (A) and sulfuryl chloride were reacted. The reaction mixture flowing out from the line mixer 19 was stored in the reaction tank 32 through the flow passage 34.

After completion of the reaction, the resulting product was analyzed by high performance liquid chromatography to find that 68.6% of the residual starting compound, 28.9% of Compound (B) and 0.5% of the by-product were contained and the remainder was impurities contained in the starting compound.

The reaction mixture stored in the reaction tank 32 was cooled to 15 to 20° C. by supplying cooling water to the jacket 33. While stirring the mixture by the stirrer 36, the valve 37 was closed, the valve 38 was opened and the constant flow rate pump 15 was driven to supply 3.5 kg of sulfuryl chloride in the storage tank 16 to the reaction tank 32 through the passage 35 over 60 minutes, whereby a reaction was carried out batchwisely.

After completion of the reaction, the resulting product was analyzed by high performance liquid chromatography to find that 0.7% of the residual starting compound, 96.0% of Compound (B) and 1.3% of the by-product were contained and the remainder was impurities contained in the starting compound.

In FIG. 3 which is shown for comparative purpose, 15 shows a constant flow rate pump, 16 shows a storage tank, 17 shows a flow passage, 18 shows a jacket, 19 shows a static mixing device, 20 shows a jacket, 22 shows a constant flow rate pump, 30 shows a storage tank, 31 shows a jacket, 32 shows a reaction tank, 33 shows a jacket, 34 shows a flow passage, 35 shows a flow passage, 36 shows a stirrer, 37 shows a valve and 38 shows a valve.

In FIG. 3, a reaction component stored in the storage tank 30 is conveyed to the static mixing device 19 by the constant flow rate pump 22. The storage tank 30 is equipped with the jacket 31 so that the reaction component stored in the storage tank 30 can be heated or cooled. Also, the static mixing device 19 is equipped with the jacket 20 so that the static mixing device 19 can be heated or cooled. In the storage tank 16, the other reaction component is stored. The storage tank 16 is equipped with the jacket 18 so that the reaction component stored in the storage tank 16 can be heated or cooled.

Simultaneously with conveying the reaction component stored in the storage tank 30 by the constant flow rate pump 22, the valve 37 is opened and the reaction component stored in the storage tank 16 is also conveyed to the static mixing device 19 by the constant flow rate pump 15. The amount of the reaction component to be conveyed is less than a necessary amount. The reaction component stored in the storage tank 30 and the reaction component stored in the storage tank 16 are reacted in the static mixing device 19, and the reaction mixture is passed through the flow passage 34 and stored in the reaction tank 32. After a predetermined amount of the reaction component stored in the storage tank 30 is conveyed, operations of the constant flow rate pump 22 and the constant flow rate pump 15 are terminated, and the valve 37 is closed. Then, the constant flow rate pump 15 is driven and the valve 38-is opened to supply the reaction component stored in the storage tank 16 to the reaction tank 32 through the flow passage 35, and the reaction is completed in the reaction tank 32. The reaction tank 32 is equipped with the jacket 33 so that the reaction tank 32 can be heated or cooled.

Example 2

A synthetic reaction was carried out by using the apparatus shown in FIG. 2. As the static mixing device 19, there was used a line mixer having the structure shown in FIG. 5 and having an inner diameter of 5 mm, a length of 150 mm, the number of elements being 18 and a distance from a first solution inlet to a second solution inlet of 20 mm.

In 35.4 l of chloroform was dissolved 20 kg of Compound (A) by heating to obtain 53.4 l of a chloroform solution containing Compound (A). The solution was charged into the storage tank 11. The solution was cooled so as to have a temperature of 35 to 40° C. by stirring it by the stirrer 13 and passing cooling water through the jacket 12.

Then, by driving the constant flow rate pump 22, the above solution was circulated through the line mixer 19 and the passage 21 until the temperature and flow of the solution became stable. By opening the valve 24 and driving the constant flow rate pump 15 so that a flow rate of 9.1 ml/min could be obtained, sulfuryl chloride in the storage tank 16 was circulated through the flow passage 23 until the flow became stable. When the respective flows became stable, the valve 24 was closed and the valve 14 was opened to supply sulfuryl chloride to the line mixer 19 at a flow rate of 9.1 ml/min and also terminate supply of cooling water to the jacket 12. Also, cooling water was supplied to the jacket 20 of the line mixer 19 to cool the reaction mixture. When 1.6 kg (0.92 l) of sulfuryl chloride was supplied, the valve 14 was closed and the valve 24 was opened to terminate supply of sulfuryl chloride, and a first stage reaction was completed.

Figure 9:
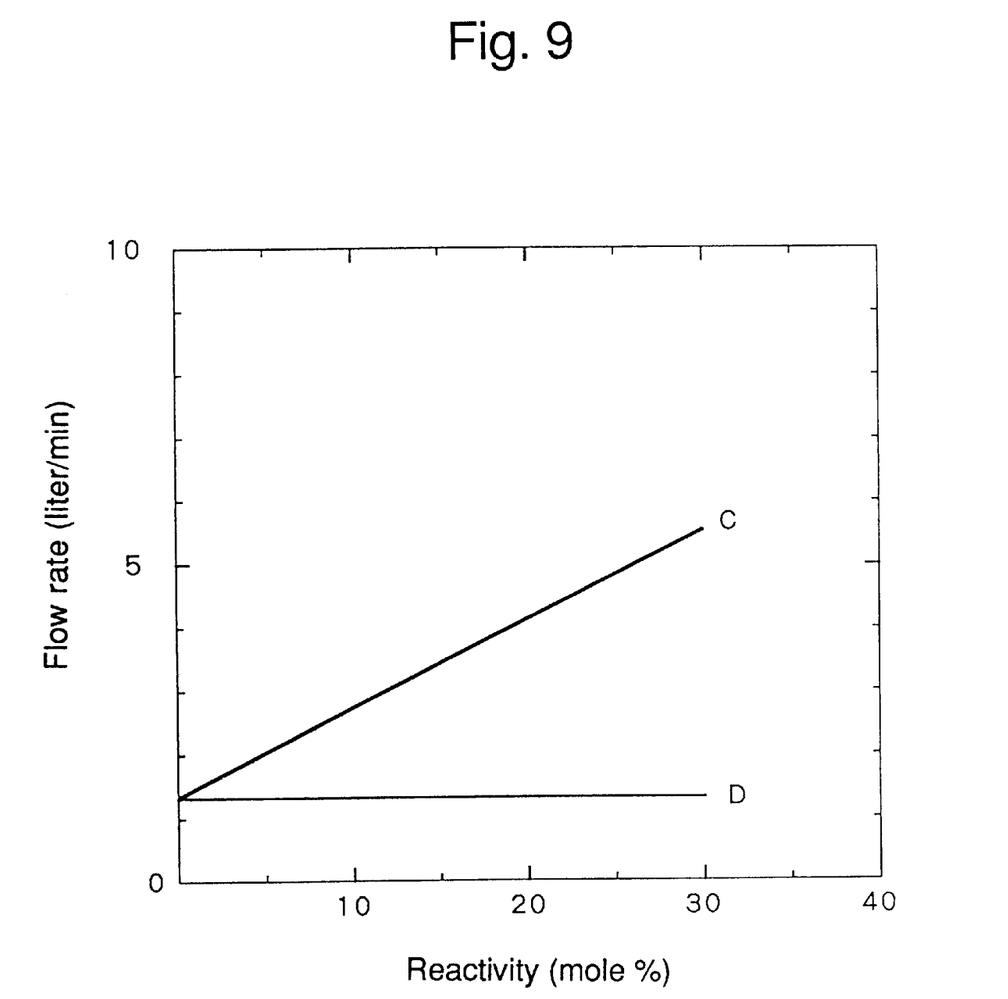
FIG. 9 is a view showing each relation between reactivity and a circulation velocity of a circulation system in Example 2 and Comparative example 2.

During the reaction, the reactivity of Compound (A) was measured by the reactivity-measuring device 26, and the constant flow rate value of the constant flow rate pump 22 was controlled so that as the reactivity was increased, the flow rate of the reaction mixture circulating through the line mixer 19 became a value shown by Curve C in FIG. 9.

After completion of the reaction, the resulting product was analyzed by high performance liquid chromatography to find that 68.6% of the residual starting compound, 28.9% of Compound (B) and 0.5% of the by-product were contained and the remainder was impurities contained in the starting compound.

The reaction mixture obtained was cooled to 15 to 20° C. By opening the valve 24 and driving the constant flow rate pump 15, sulfuryl chloride in the storage tank 16 through the flow passage 23 until the flow became stable. When the flow became stable, the valve 24 was closed and the valve 29 was opened to add 3.5 kg of sulfuryl chloride to the above reaction mixture stirred by the stirrer 13 and cooled to 15 to 20° C., through the flow passage 28 over 60 minutes, whereby a reaction was carried out batchwisely.

After completion of the reaction, the resulting product was analyzed by high performance liquid chromatography to find that 0.7% of the residual starting compound, 96.0% of Compound (B) and 1.3% of the by-product were contained and the remainder was impurities contained in the starting compound.

Comparative Example 2

A first stage reaction was carried out in the same manner as in Example 2 except for measuring the reactivity of Compound (A) during the reaction and driving the constant flow rate pump 22 so that as the reactivity was increased, the flow rate of the reaction mixture circulating through the line mixer 19 became a value shown by Curve D in FIG. 9.

After completion of the reaction, the resulting product was analyzed by high performance liquid chromatography: to find that 69.0% of the residual starting compound, 28.7% of Compound (B) and 0.6% of the by-product were contained and the remainder was impurities contained in the starting compound.

Next, a reaction was carried out batchwisely in the same manner as in Example 2. After completion of the reaction, the resulting product was analyzed by high performance liquid chromatography to find that 0.8% of the residual starting compound, 95.8% of Compound (B) and 1.4% of the by-product were contained and the remainder was impurities contained in the starting compound.

Example 3

A synthetic reaction was carried out by using the apparatus shown in FIG. 2. As the static mixing device 19, there was used a line mixer having the structure shown in FIG. 5 and having an inner diameter of 5 mm, a length of 150 mm, the number of elements being 18 and a distance from a first solution inlet to a second solution inlet of 20 mm.

In 35.4 l of chloroform was dissolved 20 kg of Compound (A) by heating to obtain 53.4 l of a chloroform solution containing Compound (A). The solution was charged into the storage tank 11. The solution was cooled so as to have a temperature of 35 to 40° C. by stirring it by the stirrer 13 and passing cooling water through the jacket 12. Then, by driving the constant flow rate pump 22, the above solution was circulated through the flow passage 21 until the temperature and flow of the solution became stable.

Figure 10:
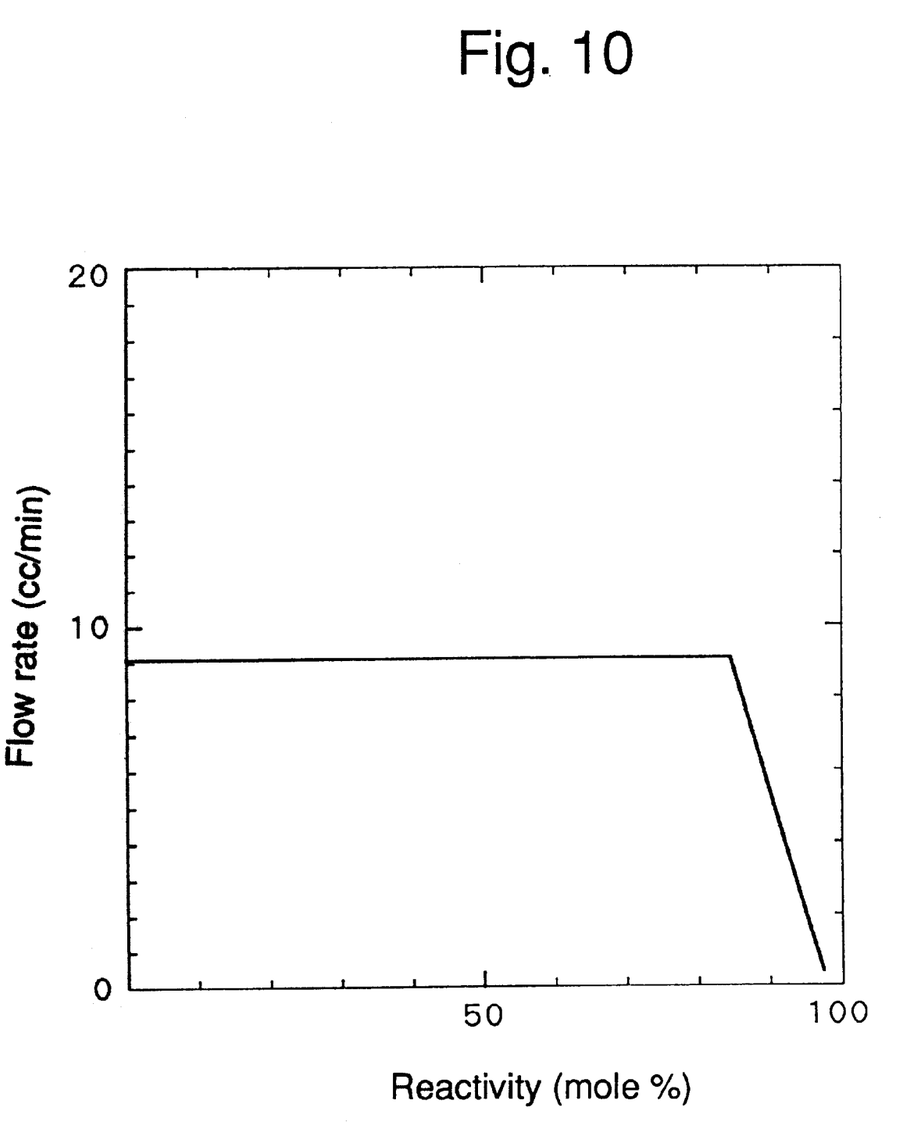
FIG. 10 is a view showing a relation between reactivity and a flow rate of sulfuryl chloride supplied to a circulation system in Example 3.
Figure 11:
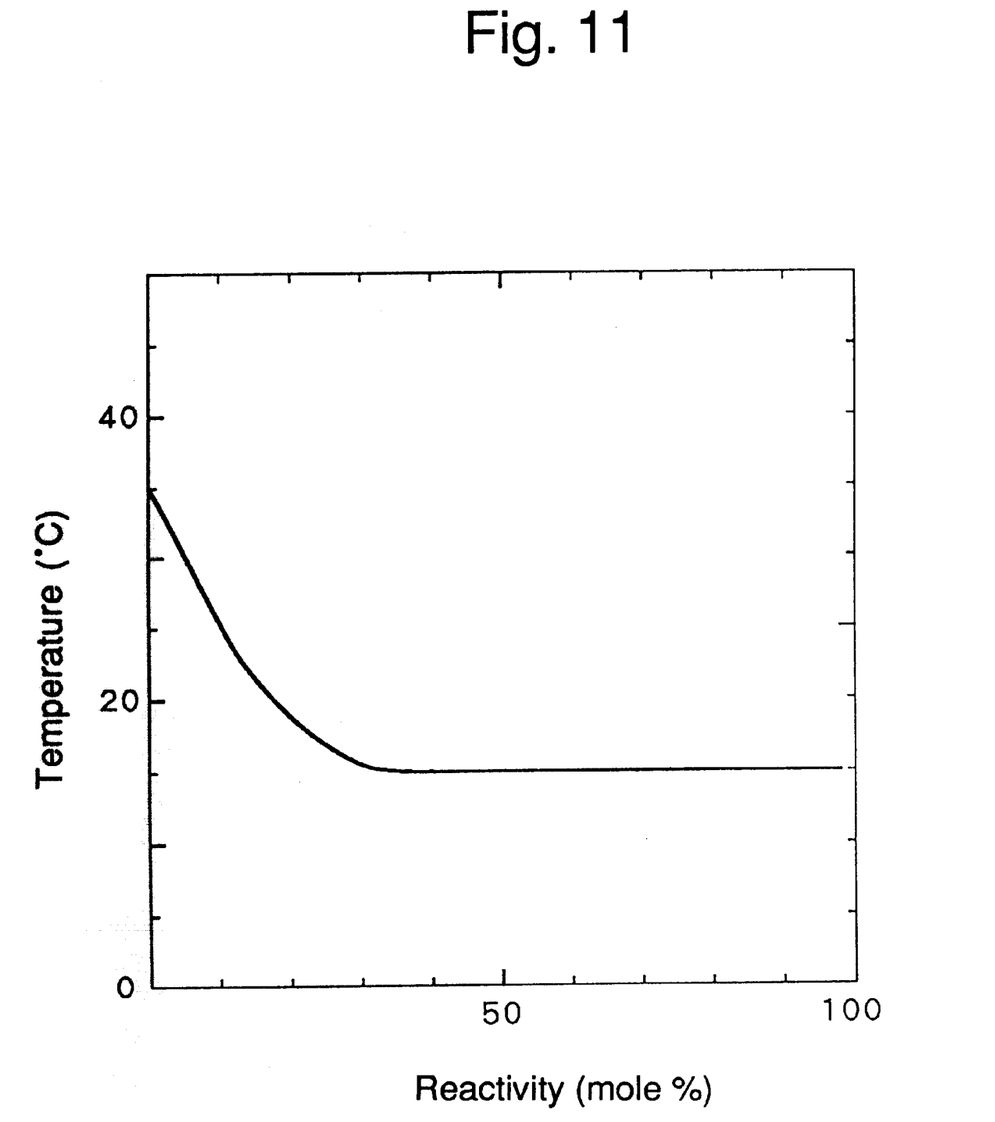
FIG. 11 is a view showing a relation between reactivity and an inner temperature of a circulation system in Example 3.

In the storage tank 16, 5.1 kg of sulfuryl chloride was stored. By opening the valve 24 and driving the constant flow rate pump 15, sulfuryl chloride in the storage tank 16 was circulated through the flow passage 23 until the flow became stable. When the respective flows became stable, the valve 24 was closed and the valve 14 was opened to supply sulfuryl chloride to the line mixer 19 at a flow rate shown in FIG. 10 which was changed depending on the reactivity, whereby a reaction was carried out. During the reaction, the reaction mixture was cooled so that the internal temperature became a temperature shown in FIG. 11 changed depending on the reactivity.

After completion of the reaction, the resulting product was analyzed by high performance liquid chromatography to find that 0.5% of the residual starting compound, 96.5% of Compound (B) and 1.0% of the by-product were contained and the remainder was impurities contained in the starting compound.

Comparative Example 3

A synthetic reaction was carried out by using the apparatus shown in FIG. 3. As the static mixing device 19, there was used a line mixer having the structure shown in FIG. 5 and having an inner diameter of 5 mm, a length of 150 mm, the number of elements being 18 and a distance from the inlet 40 to the T-shaped tube 41 of 20 mm.

In 35.4 l of chloroform was dissolved 20 kg of Compound (A) by heating to obtain 53.4 l of a chloroform solution containing Compound (A). The solution was charged into the storage tank 30. The solution was cooled so as to have a temperature of 35 to 40° C. by passing cooling water through the jacket 31.

Then, the above solution was conveyed to the reaction tank 32 through the line mixer 19 by driving the constant flow rate pump 22 so that a flow rate of 1.3 l/min could be obtained.

In the storage tank 16, 5.1 kg of sulfuryl chloride was stored. By driving the constant flow rate pump 15, sulfuryl chloride was supplied to the line mixer 19 through the flow passage 17 at a flow rate of 70.8 cc/min to carry out a reaction. The reaction mixture flowing out from the line mixer 19 was stored in the reaction tank 32 through the flow passage 34.

After completion of the reaction, the resulting product was analyzed by high performance liquid chromatography to find that 3.7% of the residual starting compound, 90.0% of Compound (B) and 4.2% of the by-product were contained and the remainder was impurities contained in the starting compound.

According to the mixing method of the present invention, a desired compound can be obtained with high yield by suppressing generation of a by-product while reducing a production cost.

We claim:

1. A process for forming a compound comprising the steps of:

circulating a first solution including a first component and contained in a vessel along a circulation route connected to the vessel;

supplying a second solution including a second component into a static mixing device provided in the circulation route to mix the first solution with the second solution to form a compound during circulation;

monitoring an amount of the compound in the circulation route;

supplying the second solution into the vessel after supplying the second solution into the static mixing device; and controlling at least one of a flow velocity of the second solution, a temperature of the circulation route, and a circulation velocity of the circulation route according to the results of said monitoring step.

2. The process of claim 1, wherein the first and second solution are flowed into the static mixing device.

3. An apparatus for forming a compound comprising:

a vessel for introducing a first solution including a first component;

a circulation route connected with the vessel and through which the first solution is circulated;

a static mixing device arranged in the circulation route;

a first supplier for supplying a second solution including a second component into the static mixing device;

a second supplier for supplying the second solution into the vessel;

a monitor having an output representing an amount of a compound in the circulation route; and a controller for controlling a flow velocity of the second solution, a temperature of the circulation route, or a circulation velocity of the circulation route according to the output of said monitor.

4. The apparatus of claim 3, wherein the first and second solutions are flowed into the static mixing device.

* * * * *